US009784742B2

(12) United States Patent
Benz et al.

(10) Patent No.: US 9,784,742 B2
(45) Date of Patent: Oct. 10, 2017

(54) MEANS AND METHODS FOR NON-INVASIVE DIAGNOSIS OF CHROMOSOMAL ANEUPLOIDY (75) Inventors: Marcus Benz, Constance (DE); Wera Hofmann, Constance (DE); Thomas Pohl, Constance (DE); Christoph Von Kalle, Schallstadt (DE)

(73) Assignee: LifeCodexx, Constance (DE)

( * ) Notice: Subject to any disclaimer, the term of this patent is extended or adjusted under 35 U.S.C. 154(b) by 957 days.

(21) Appl. No.: 13/502,498

(22) PCT Filed: Oct. 26, 2010

(86) PCT No.: PCT/EP2010/066161
§ 371 (c)(1),
(2), (4) Date: Sep. 7, 2012

(87) PCT Pub. No.: WO2011/051283
PCT Pub. Date: May 5, 2011

(65) Prior Publication Data
US 2013/0017958 A1 Jan. 17, 2013

Related U.S. Application Data (60) Provisional application No. 61/272,722, filed on Oct. 26, 2009.

(51) Int. Cl.
C12Q 1/68 (2006.01)
G01N 33/574 (2006.01)
G06F 19/22 (2011.01)

(52) U.S. Cl.
CPC ......... *G01N 33/574* (2013.01); *C12Q 1/6806* (2013.01); *C12Q 1/6851* (2013.01); *G01N 2800/368* (2013.01); *G01N 2800/385* (2013.01); *G06F 19/22* (2013.01)

(58) Field of Classification Search
None
See application file for complete search history.

(56) References Cited

FOREIGN PATENT DOCUMENTS

| WO | WO 2007/121276 A2 | 10/2007 |
| WO | WO 2009/013496 A1 | 1/2009 |
| WO | WO 2009/097511 | 8/2009 |
| WO | WO 2010/033578 A2 | 3/2010 |

OTHER PUBLICATIONS

Swarup et al., "Circulating (cell-free) Nucleic Acids—A Promising, non-invasive Tool for Early Detection of Several Human Diseases," *FERS Letters* 581, pp. 795-799 (2007).
Bremnes et al., "Circulating Tumour-Derived DNA and RNA Markers in Blood: A Tool for Early Detection, Diagnostics, and Follow-up?," *Lung Cancer*, vol. 49, pp. 1-12 (2005).
Muller et al., "Identification of Loss of Heterozygosity on Circulating Free DNA in Peripheral Blood of Prostate Cancer Patients: Potential and Technical Improvements," *Clinical Chemistry*, pp. 688-696 (2008).
Barski et al., "High-Resolution Profiling of Histone Methylatons in the Human Genome," *Cell*, vol. 129, pp. 823-837 (2007).
Chan et al., "Hypermethylated RASSFIA in Maternal Plasma: A Universal Fetal DNA Marker that Improves the Reliability of Noninvasive Prenatal Diagnosis," *Clinical Chemistry*, vol. 52, No. 12, pp. 2211-2218 (2006).
Chiu et al., "Noninvasive prenatal diagnosis of fetal chromosomal aneuploidy by massively parallel genomic sequencing of DNA in maternal plasma," *PNAS*, vol. 105, No. 51, pp. 20458-20463 (2008).
Dhallan et al., "Methods to Increase the Percentage of Free Fetal DNA Recovered from the Maternal Circulation," *JAMA*, vol. 291, No. 9, pp. 1114-1119 (2004).
Emani et al., "Agilent's SureSelect Target Enrichment System: Bringing Cost and Process Efficiency to Next-Generation Sequencing," 7 pages (2010).
Costa, et al., "New Strategy for Prenatal Diagnosis of X-Linked Disorders," *N. Engl.J. Med.*, vol. 346, p. 1502 (2002).
Fan, et al., "Noninvasive diagnosis of fetal Aneuploidy by shotgun sequencing DNA from maternal blood," *PNAS*, vol. 105, No. 42, pp. 16266-16271 (2008).
Fan et al., "Detection of Aneuploidy with Digital Polymerase Chain Reaction," *Analytical Chemistry*, pp. 7576-7579 (2007).
Fields, "Site-Seeing by Sequencing," *Science*, vol. 316, pp. 1441-1442 (2007).
Gnirke et al., "Solution Hybrid Selection with Ultra-long Oligonucleotides for Massively Parallel Targeted Sequencing," *Nat Biotechnol.*, vol. 27, No. 2, pp. 182-189 (2009).
Jorgez et al., "Improving Enrichment of Circulating Fetal DNA for Genetic Testing: Size Fractionation Followed by Whole Gene Amplification," *Fetal Diagn. Ther.*, vol. 25, pp. 314-319 (2009).
Johnson et al., "Genome-Wide Mapping of in Vivo Protein-DNA Interactions," *Science*, vol. 316, pp. 1497-1502 (2007).
Li et al., "Fast and Accurate Short Read Alignment with Burrows-Wheeler Transform," *Bioinformatics*, pp. 1754-1760 (2009).
Lo et al., "Prenatal diagnosis: progress through plasma nucleic acids," *Genetics*, vol. 8, pp. 71-77 (2007).
Lo et al., "Noninvasive Prenatal Diagnosis of Fetal Chromosomal Aneuploidies by Maternal Plasma Nucleic Acid Analysis," *Clin. Chem*, vol. 54, No. 3, pp. 461-466 (2008).
Lo et al., "Presence of fetal DNA in Maternal Plasma and Serum," *Lancet*, vol. 350, pp. 485-487 (1997).
Lo et al., "Digital PCR for the molecular detection of fetal chromosomal aneuploidy," *PNAS*, vol. 104, No. 32, pp. 13116-13121 (2007).
Lo et al., "Quantitative Analysis of Fetal DNA in Maternal Plasma and Serum: Implications for Noninvasive Prenatal Diagnosis," *Am. J. Hum. Genet.*, vol. 62, pp. 768-775 (1998).
Lo et al., "Prenatal Diagnosis of Fetal RhD Status by Molecular Analysis of Maternal Plasma," *The New English Journ. Of Med.*, pp. 1734-1738 (1998).

(Continued)

*Primary Examiner* — Nancy Treptow
(74) *Attorney, Agent, or Firm* — Foley & Lardner LLP (57) ABSTRACT

The invention relates to a prenatal diagnostic method for the determination of a fetal chromosomal aneuploidy in a biological sample obtained from a pregnant woman, which method comprises enrichment and quantification of selected cell-free deoxyribonucleic acid sequences showing consensus nucleosome binding regions.

9 Claims, 8 Drawing Sheets (56) References Cited

OTHER PUBLICATIONS

Malone et al., "First-Trimester or Second-Trimester Screening, or Both, for Down's Syndrome," *The New Engl. Journ. Of Med.*, vol. 353, No. 19, pp. 2001-2011 (2005).
Mikkelsen et al., "Genome-wide maps of chromatin state in pluripotent and lineage-committed cells," *Nature*, vol. 448, No. 7153, pp. 553-560 (2007).
Parameswaran, et al., A pyrosequencing-tailored nucleotide barcode design unveils opportunities for large-scale sample multiplexing, *Nucleic Acids Research*, vol. 35, No. 19, 9 pages (2007).
Margulies et al., "Genome Sequencing in Open Microfabricated High Density Picoliter Reactors," *Nature*, vol. 437, No. 7057, pp. 376-380 (2005).
Robertson et al., "Genome-Wide Profiles of STAT1 DNA associated using chromatin immunoprecipitation and massively parallel sequencing," *Nature Methods*, vol. 4, No. 8, pp. 651-657 (2007).
Schones et al., "Dynamic Regulation of Nucleosome Positioning in the Human Genome," *Cell*, vol. 132, pp. 897-898 (2008).
Wright et al., "The use of cell-free fetal nucleic acids in maternal blood for non-invasive prenatal diagnosis," *Human Reproduction Update*, vol. 15, No. 1, pp. 139-151 (2009).
Wu et al., "Chromosome 5 Aberrations and Genetic Predisposition to Lung Cancer," *Int. J. Cancer.*, vol. 79, pp. 490-493 (1998).
International Preliminary Report on Patentability cited in related International Patent Application No. PCT/EP2010/066161, completed May 10, 2012.
International Search Report cited in related International Patent Application No. PCT/EP2010/066161, completed Mar. 4, 2011.
Written Opinion cited in related International Patent Application No. PCT/EP2010/066161, completed Mar. 4, 2011.

MEANS AND METHODS FOR NON-INVASIVE DIAGNOSIS OF CHROMOSOMAL ANEUPLOIDY

The present invention relates to a non-invasive prenatal detection method in a biological sample obtained from a pregnant woman. In particular, the invention relates to a method for non-invasive prenatal diagnosis (NIPD) by enrichment and quantification of selected cell-free deoxyribonucleic acid sequences in a maternal blood sample, to detect fetal chromosomal abnormalities, e.g. fetal chromosomal aneuploidies.

In many countries prenatal diagnosis of fetal aneuploidies as well as single gene Mendelian disorders, such as cystic fibrosis, are typically part of public health programs. The obstetrics care includes particularly non-invasive prenatal testing such as first trimester screening or second trimester screening to risk-stratify pregnant women prior to invasive diagnostic procedures. These screening tests usually include a blood test estimating biochemical markers and an ultrasound examination to measure fetal nuchal translucency with an accuracy of up to 90% (Malone et al. 2005 *N Eng J Med* 353, 2001-2011). Invasive procedures, including amniocentesis, chorionic villus sampling or cordocentesis, are used to obtain direct fetal genetic material (and perform karyotype analysis) and achieve over 99% accuracy. However, these invasive procedures pose a potential risk of fetal loss. There is currently great interest in the development of methods for direct but non-invasive diagnosis of fetal genetic disease with the absence of risk of miscarriage.

The discovery of cell-free fetal nucleic acids in maternal plasma has opened up new possibilities for non-invasive prenatal diagnosis. (Lo, Y M D et al. 1997 *Lancet* 350, 485-487; Lo, Y M D and Chiu, R W K 2007 *Nat Rev Genet* 8, 71-77). Over the last few years, this approach has been applied to the prenatal diagnosis of sex-linked (Costa, J M et al. 2002 *N Engl J Med* 346, 1502) and certain single gene disorders (Lo, Y M D et al. 1998 *N Engl J Med* 339, 1734-1738). Other applications involve the enrichment of fetal DNA by a method that suppresses the maternal background, such as by the addition of formaldehyde (Dhallan, R et al. 2004 *JAMA* 291, 1114-1119) or the targeting of fetal-specific nucleic acid molecules, including fetal-specific epigenetic markers and placenta-specific mRNA markers (Chan, K C et al. *Clin Chem* 2006; 52:2211-8).

Recent reports have indicated that the development of highly discriminatory quantitative methods for chromosome dosage analysis using digital polymerase chain reaction technology may be useful for the non-invasive detection of fetal aneuploidies by the analysis of cell-free DNA and RNA in maternal plasma or serum (Fan, H C and Quake, S R 2007 *Anal Chem* 79, 7576-7579; Lo, Y M D et al. 2007 *PNAS* 104, 13116-13121). But the low fraction of fetal nucleic acids co-existing in maternal plasma with a high background of nucleic acids of maternal origin can often interfere with these analyses (Lo, Y M D et al. 1998 *Am J Hum Genet* 62, 768-775).

With the rapid development of high-throughput sequencing technology allowing massively parallel sequencing of tens of millions of short sequencing tags, the possibility of detecting the presence of trisomy fetal genomes in the maternal plasma DNA sample obtained in the first trimester of pregnancy has recently been explored. (Fan, H C et al. 2008 *PNAS* 105, 16266-16271; Chiu, R W et al. 2008 *PNAS* 105, 20458-20463). This shotgun sequencing technology enables a deeper sampling than can be achieved by digital PCR. However, the costs of DNA sequencing using shotgun sequencing are too high to bring this approach in a routine medical test as part of prenatal care.

In addition, a technical drawback of random shotgun sequencing is the potential risk to introduce sequence bias. The random shotgun sequencing cannot output a perfectly even read distribution across a genome of interest so that statistically there will always be some stretches of DNA that are read out more than others.

WO 2009/013496 refers to a non-invasive method for prenatal diagnostic testing of a fetal chromosomal aneuploidy by determining imbalances between different nucleic acid sequences in a maternal sample by massively parallel genomic sequencing (MPGS).

Accordingly, there is a strong need for a less costly and less time intensive non-invasive method for prenatal diagnosis of a fetal chromosomal abnormality e.g. a fetal chromosomal aneuploidy, in a biological sample obtained from a pregnant woman, which method has a high sensitivity and specificity and does not introduce any further sequence bias.

It is thus an objective of the present invention to provide an alternative, improved method for performing prenatal diagnosis.

More specifically, the invention relates to a method for the determination of a fetal chromosomal aneuploidy in a biological sample obtained from a pregnant female individual, wherein the biological sample includes nucleic acid molecules, the method comprising:
a) selecting for and isolating from a biological sample of a pregnant female individual one or more target sequences of DNA molecules contained in the biological sample, wherein said target sequences comprise DNA sequences having consensus nucleosome binding regions;
b) amplifying said selected target sequences;
c) sequencing said amplified selected target sequences and allotting them to chromosomes of the genome and identifying the unique allotted target sequences;
d) determining a first amount each of one or more first chromosomes identified on the basis of said amplified unique target sequences originating from said one or more first chromosomes;
e) determining a second amount each of one or more second chromosomes identified on the basis of said amplified unique target sequences originating from said one or more second chromosomes; and
f) determining based on the said first and second amount a fetal chromosomal aneupoidy of one or more of said first chromosomes.

The aforementioned method may or may not comprise additional steps prior, after or in between the explicitly mentioned essential steps of the method. Preferably, the method encompasses steps of obtaining the biological sample from a pregnant female individual. Moreover, the method may preferably encompass sample pre-treatment steps which, e.g., aim to preserve the nucleic acids present in the sample or which aim to release or isolate the nucleic acids from cellular material present in the sample The method may be, preferably, assisted by automation. The steps a) to c) may be assisted by a robotic device, the remaining steps evaluating the sequence data may be assisted by a computer or data processing device having tangibly embedded an algorithm for determining the amounts of the sequences and for carrying out the comparison.

The term "fetal chromosomal aneuploidy" as used herein refers to chromosomal aberration which is characterized by a number of chromosomes which differs from the physiological number of chromosomes which are expected to be present in a fetus, i.e. an abnormal number of chromosomes. Such a difference in the number is also referred to as numerical aberration. The term encompasses an increased number of a chromosome as well as a decreased number of a chromosome present in the fetal genome. A chromosomal aneuploidy as referred to in the context of the present invention may be (i) a monosomy, i.e. the lack of chromosome of a chromosome pair, (ii) a disomy in cases where the individual to be examined is normally triploid, tetraploid or even more, or an uniparenteral disomy, (ii) a trisomy, i.e. the presence of three instead of two chromosomes which are physiologically present for each chromosome in a diploid organism, (iv) a tetrasomy, i.e. the presence of four chromosomes instead of two chromosomes which are physiologically present for each chromosome in a diploid organism or even (v) a pentasomy, i.e. the presence of five chromosomes instead of two chromosomes which are physiologically present for each chromosome in a diploid organism. The aneuploidy can affect either the autosomes or the gonosomes. In some cases a chromosome pair may be even entirely missing in the genome. Moreover, an aneuploidy as used herein also encompasses a numerical aberration with respect to a part of a chromosome, i.e. a case where a part of one of the chromosomes of a chromosome pair is deleted or present in one or more extra copies. A part of a chromosome may be present in an inappropriate number of copies as a result of a structural aberration, e.g., unbalanced translocations, contiguous gene syndromes or chromosomal deletion syndromes. Fetal chromosomal aneupoidy usually results in severe disorders or diseases affecting the fetus and its development. Preferred fetal chromosomal aneuploidies and accompanying diseases or disorders which can be determined by the method of the present invention include Turner syndrome (gonosomal monosomy), Klinefelter syndrome (XXY gonosomes), triple-X syndrome (XXX gonosomes), Down syndrome (Trisomy 21), Edwards syndrome (Trisomy 18) or Patau syndrome (Trisomy 13). Uniparenteral disomy is known for chromosome 15 as Prader-Willi-Syndrome. If such a uniparenteral disomy is to be detected, the analysed DNA must also be distinguished in to paternally inherited or maternally inherited DNA. Unbalanced translocations as used herein encompass, preferably, unbalanced Robertson trisomy, rob(13q;14q). Other structural aberrations which can be preferably determined by the method of the invention include 4q-deletion (Wolf-Hirschhorn syndrome), 5q-deletion (cri du chat syndrome) or microdeletion syndromes, in particular, 17q11.2 deletion (Smith-Magenis syndrome) or 22q11.2 deletion (DiGeorge syndrome).

The phrase "determination of a fetal chromosomal aneuploidy" as used herein refers to assessing the probability according to which a subject is suffering or will suffer from a disease or condition referred to in this specification. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population.

The term "individual" as used herein refers to a multicellular organism which is capable of carrying its offspring inside an uterus. More preferably, said organism refers to eutheric organisms and, more preferably, to mammals. Most preferably, the individual is a human. It will be understood that the individual a sample of which is applied in the method of the present invention shall be a pregnant female carrying an embryo or fetus inside its uterus. During pregnancy and particular the fetal stages of the embryonic development, fetal genomic DNA is released into the body of the female individual. In particular, such fetal gemoic DNA occurs in the blood of the female individual.

Thus, the term "biological sample" as used herein refers to a sample from a individual, preferably, to a sample of a body liquid obtained from a pregnant woman. More preferably, said body liquid is selected from the group consisting of a blood sample, a urine sample and a saliva sample. The blood sample referred to herein encompasses a whole blood sample, a plasma sample or a serum sample. It will be understood that the sample to be used in the method of the present invention shall comprise nucleic acids and, in particular, DNA molecules being representative for the genome of the developing fetus. Preferably, the said fetal genome derived DNA molecules equally represent each chromosome present in the said fetal genome in a statistical manner. Thus, the more copies of a given chromosome are present in the fetal genome, the more DNA molecules will reflect these chromosomes in the sample and vice versa.

The DNA molecules present in the sample including the fetal genome derived DNA molecules are specifically selected for DNA molecules comprising target sequences allowing for a meaningful an efficient sequence analysis in the context of the present invention. Suitable target sequences comprise consensus sequences for nucleosome binding regions as specified elsewhere herein or matrix attachment regions of the chromosomal DNA. The term "consensus nucleosome binding region" as used herein refers to DNA sequence patterns at or around transcription start sites (TSS) of transcribed genes that are associated with well-positioned nucleosomes located at or near such transcription start sites. Suitable consensus sequences are known in the art and are described in Schones et al. or Fan et al. (Schones 2008, Cell 132(5): 887-898, Fan 2008, Proc. Natl. Acad. Sci. USA 105: 16266-16271).

Selecting and isolating such DNA molecules comprising target sequences for the sequence analysis as used herein includes the provision of suitable sequences for primers used for DNA amplification. Preferably, suitable sequences are provided by ligating adapter oligonucleotides comprising suitable sequences for DNA amplification to the DNA molecules. Preferably, the adapter oligonucleotides can also comprise additional sequences, preferably, barcode or index tag sequences which allow for identification of a pool of identical DNA molecule species. (see Parameswaran 2007, Nucl. Acids Res. 35(19): e130). By using such adaptor oligonucleotides comprising barcode or index tag sequences, it is possible to process a pool of DNA molecules of different samples in the method of the present invention in parallel. Moreover, the term also encompasses isolation and enrichment procedures for DNA molecules comprising such target sequences using, e.g., affinity chromatograph or batch-wise enrichment using labled nucleic acid baits which allow for enrichment and isolation of hybridized DNA molecules by affinity purification, e.g., via magnetic beads. In a preferred embodiment of the method of the present invention, biotinylated RNA bait molecules are brought into contact with the DNA molecules comprised by the sample. The RNA bait molecules are specifically designed to have a sequence which is capable of hybridizing to the target sequence of the desired DNA molecules, in particular, they have sequences capable of hybridizing to the consensus sequences for nucleosome binding regions as specified elsewhere herein or matrix attachment regions of the chromosomal DNA. After hybridization, the chimeric DNA/RNA hybrid molecules are isolated from the remaining sample by capture of the biotin lable via streptavidin. Preferably, magnetic beads with immobilized streptaviding can be applied for the isolation. The isolated DNA molecules can be released from the magnetic beads. Depending on how the release is carried out, enrichment of the DNA molecules may also occur. A particular suitable techniques for isolating and enriching the desired DNA molecules is the commercially available SureSelect Target Enrichment System from Agilent Technologies, Inc., US. Details are also found in Gnirke 2009, Nat Biotechnology 27(2): 182-189 hereby also incorporated by reference. Subsequently, the said isolated DNA molecules comprising the target sequence can be further processed according to the method of the invention. Another particular technique is the four-color DNA sequencing-by-synthesis technology from Illumina, Inc., US (see Johnson 2007, Science 316: 1497-1502; Robertson 2007, Nature Methods 4: 651-657; Barski 2007, Cell 129: 823-837; Mikkelsen 2007, Nature 448: 553-560; Fields 2007, Science 316: 1441-1442).

Amplification of the target sequence comprising DNA molecules can be achieved by the well known methods for nucleic acid amplification. Preferably, amplification is carried out by PCR. Sequencing of the amplification products can be done by the well known techniques for nucleic acid sequencing. Quality of the analyzed samples may be assured after amplification. Moreover, DNA molecules in the sample may be allocated into DNA molecules with sequences of paternal or maternal origin.

Preferably, paternal sequences are analyzed when fetal genomes shall be analyzed by the method of the present invention. By analyzing such paternally inherited DNA molecules, the reliability of the method may be further improved since such sequence unambiguously originate from the fetal genomic DNA.

The sequences identified by the sequencing of the amplified DNA molecules comprising the desired target sequences can be allocated to chromosomes or parts thereof by the presence of characteristic sequences of said chromosomes. Suitable sequences which allow for allocation are genetic marker sequences, for example, by single sequence polymorphism markers, repetitive DNA marker sequences such as single sequence repeats, short tandem repeats, variable number tandem repeats or microsatellite sequences in general. Alternatively, the allocation can be made by sequence comparison with consensus sequences for chromosomes such as the hg18 or hg19 consensus sequences for the human genome. After the target sequences have been allocated to a chromosome, i.e. after mapping of the target sequences to the chromosomes, the unique alloted target sequences, i.e. the target sequences which have only once been allocated to a chromosome, among the mapped target sequences are identified. Suitable algorithms for sequence comparison and allocations to chromosomes include Efficient Local Alignment of Nucleotide Data (ELAND; an alignment tool integrated in Illumina-Solexa data processing package, enable ungapped alignment for reads with size up to 32 bp; Cox, unpublished) or Burrows-Wheeler Aligner (BWA; Li and Durbin 2009, Bioinformatics 25:1754-1760).

In a subsequent step, a first amount for each of one or more first chromosomes identified on the basis of said unique allotted target sequences originating from said one or more first chromosomes is determined. Said amount can be any number or value which reflects or correlates to the number of the unique target sequences being allocated to a chromosome which have been obtained from the DNA molecules. The amount may be an absolute or relative amount, i.e. a normalized amount, e.g., with respect to the total number of amplified target sequences and/or the total amount of nucleic acids found in the sample. Simultaneously or separately, a second amount for each of one or more second chromosomes identified on the basis of said unique alloted target sequences originating from said one or more second chromosomes is determined.

Based on the said first and second amount a fetal chromosomal aneuploidy of one or more of said first chromosomes can be determined. This can be done for, e.g., a diploid individual by comparing a relative first amount of a first chromosome to a relative second amount of a second chromosome. In case of a diploid individual the relative first and second amounts shall be essentially identical. A increased relative first amount with respect to the second amount, shall be indicative for an increased number of the first chromosome and, thus, an aneuploidy of the first chromosome in the fetal genome. The same applies mutatis mutandis for a reduced first amount. Preferably, in humans, chromosomes 1, 2, 3, 5 to 15, 18 and 21 can be used for deriving a second amount as referred to above.

Also preferably, a parameter can be determined based on the first and the second amounts. Such a parameter shall be statistically more robust and allows for comparison between different individuals or collectives of individuals.

Thus, in a preferred embodiments of the method of the present invention, said method further comprises:
i) determining a parameter from said first amount relative to said second amount;
ii) comparing the parameter to a corresponding cut off control value; and based on the comparison, determining whether or not there is a difference allowing for the prediction of a fetal chromosomal aneuploidy of one or more of said first chromosomes.

The term "parameter" as used herein refers to a numerical value that characterizes a quantitative data set and/or a numerical relationship between quantitative data sets. More specifically, said parameter may be calculated as a ratio of the first amount and the second amount or may be a value derived from said ration such as a percentage value. Preferably, the parameter reflects the amount of a first chromosome to be investigated with respect to the amount(s) of at least one other second chromosome and, preferably, with respect to the remaining chromosomes as determined by the target sequences. Moreover, the parameter may be even made more robust with respect to individual variations and, thus, suitable for comparison with parameters from reference individuals or groups thereof. To this end, a parameter which has been calculated as set forth above (reference parameter) may be, preferably, subtracted from the determined parameter and divided by the standard deviation for the reference parameter. The resulting transformed parameter, also termed "z-score" (see Chiu 2008, Proc Natl. Acad Sci USA 105(51):20458-63), can then be compared to a transformed parameter from a reference individual or group of individuals known to exhibit the chromosomal aneuploidy or known not exhibit the said aneuploidy. The reference parameter thus constitutes a cut off value and based on the comparison, it is possible to determine whether or not there is a difference in the number of chromosomes of the fetal genome allowing for the prediction of a fetal chromosomal aneuploidy of one or more of said first chromosomes. The term "cut off value" or "cut off control value" as used herein, preferably, refers to a numerical value calculated as the ratio of two quantities of chromosomes relative to each other, i.e. the ratio of the amount of one or more first chromosomes relative to the amount of one or more second chromosomes of an average or pooled blood, urine or saliva sample of one or more healthy female donors, and wherein the number of said second chromosomes is identical with the number of said first chromosomes to be compared with. The cut off value allows to distinguish between a diseased and non-diseased state of an experimental biological sample. Further techniques for determining parameters and comparing them between different individuals or groups thereof which can be preferably applied in the method of the present invention are those that have been described in EP 2 183 692 A1, EP 2 183 693 A1 or WO2010/033578.

It was recently found by Fan et al. (Fan 2008, loc.cit) that cell-free plasma DNA is mainly apoptotic in origin and shares features of nucleosomal DNA. Thus, according to the present invention the non-invasive method for prenatal diagnosis disclosed in WO 2009/013496 was further developed and improved by suggesting carrying out an additional enrichment step before the step of sequencing to capture and specifically enrich selected DNA regions showing consensus nucleosome positions on the chromosomes of interest. By this modification of the state-of-the-art method, the cost- and process efficiency can be substantially improved and particularly as compared to massively parallel genomic sequencing using random shotgun sequencing. The present target enrichment process offers significant increase in speed and additional advantages in scalability over current polymerase chain reaction (PCR) techniques in most next-generation sequencing workflows. It is based on an efficient hybrid selection technique which improves cost and process efficiency of the so-called "massively parallel genomic sequencing" workflow (Gnirke, A et al. 2009 *Nat Biotechnol* 27, 182-189). The analysis of multiple sets of specific target loci is used to increase the amount of data obtainable from a sample without increasing the number of (digital) PCR sampling performed for subsequent massively parallel genomic sequencing, such as that achievable by 454 technology (Roche).

The method according to the present invention is suitable for determining in a blood sample from a pregnant individual the chromosomal aneuploidy of the developing offspring. In particular, a chromosomal aneuploidy of a developing fetus can be determined, particularly, as from the 6th week of gestation onwards.

The present invention also relates to a method for the determination of a chromosomal aberration in a biological sample obtained from an individual, wherein the biological sample includes nucleic acid molecules, the method comprising:
a) selecting for and isolating from said biological sample of an individual one or more target sequences of DNA molecules contained in the biological sample, wherein said target sequences comprise DNA sequences having consensus nucleosome binding regions;
b) amplifying said selected target sequences;
c) sequencing said amplified selected target sequences and allotting them to chromosomes of the genome and identifying the unique allotted target sequences;
d) determining a first amount each of one or more first chromosomes identified on the basis of said unique allotted target sequences originating from said one or more first chromosomes;
e) determining a second amount each of one or more second chromosomes identified on the basis of said unique allotted target sequences originating from said one or more second chromosomes; and
f) determining based on the said first and second amount a chromosomal aberration.

The term "chromosomal aberration" as used herein, preferably, refers to numerical aberrations as defined elsewhere herein.

Preferably, step f) of said method further comprises:
i) determining a parameter from said first amount relative to said second amount;
ii) comparing the parameter to a corresponding cut off control value; and based on the comparison, determining whether or not there is a difference wherein the presence of a difference is indicative for a chromosomal aberration in one or more of said first chromosomes.

More preferably, the chromosomal aberration shall be indicative for a predisposition for cancer.

The term "predisposition" as used herein refers to an increased risk that an individual will develop cancer within a certain predictive window in the future. Preferably, said window is up to 1 year, up to 5 years, up to 10 years or the entire life span of the individual.

The term "cancer" as used herein encompasses any malignant neoplasm. Different cancer types are well known in the art. Preferably, the cancer referred to in accordance with the present invention is associated with chromosomal aberration. In particular, the following cancers have been reported to be frequently associated with chromosomal aberrations are selected from the group consisting of: human leukemias such as acute myeloid leukaemia or chronic myeloid leukemia (see, e.g. Mitelman Database of Chromosome Aberrations and Gene Fusions in Cancer (2010). Mitelman F, Johansson B and Mertens F (Eds.), cgap.nci.nih.gov/Chromosomes/Mitelman).

Preferably, said individual in context of the aforementioned method is an individual as defined elsewhere herein and, most preferably, it is a human.

Preferably, said biological sample comprises a cell suspected to be a cancer cell. Suitable samples can be obtained from body fluids in the case of non-solid tumors, e.g., blood in the case of hematopoietic cancers, or from tissue biopsy samples. Depending on the type of cancer, the person skilled in the art knows how to obtain a sample comprising cells suspected to be cancer cells.

The present invention contemplates a computer programme product which when executed on a computer or data processing device is capable of carrying out the following steps:
a) allotting amplified selected and isolated target sequences having consensus nucleosome binding regions from a biological sample of an individual to chromosomes of the genome and identifying unique allotted target sequences;
b) determining a first amount for each of one or more first chromosomes identified on the basis of said unique allotted target sequences originating from said one or more first chromosomes; and
c) determining a second amount for each of one or more second chromosomes identified on the basis of said unique allotted target sequences originating from said one or more second chromosomes; and d) determining based on the said first and second amount a fetal chromosomal aneupoidy of one or more of said first chromosomes or a chromosomal aberration.

In a preferred embodiment of said computer programme product of said determining in step d) further comprises:
i) determining a parameter from said first amount relative to said second amount;
ii) comparing the parameter to a corresponding cut off control value; and based on the comparison, determining whether or not there is a difference allowing for the prediction of a chromosomal aberration in one or more of said first chromosomes or determining whether or not there is a difference allowing for the prediction of a fetal chromosomal aneuploidy of one or more of said first chromosomes.

Finally, the present invention contemplates a device for carrying out a method of the present invention comprising:
a) an analyzing unit comprising a subunit capable of selecting for and isolating from said biological sample of an individual one or more target sequences of DNA molecules contained in the biological sample, wherein said target sequences comprise DNA sequences having consensus nucleosome binding regions, a subunit for amplification of said target DNA molecules and a subunit for sequencing of amplified target sequences; and
b) an evaluation unit comprising a receiving subunit for the sequence data and a computer or data processing subunit executing the computer programme product of the present invention.

The term "device" as used herein relates to a system comprising at least the aforementioned analyzing unit and the evaluation unit operatively linked to each other. How to link the units of the device in an operating manner will depend on the type of units included into the device. For example, where units for automatic analysis of a sample are applied, the data obtained by said automatically operating analyzing unit can be processed by the computer program product of the evaluation unit in order to obtain the desired diagnostic results. Preferably, the units are comprised by a single device in such a case. However, the device may also comprise physically separate units which are connected by wire, wireless or via the internet.

All references cited in this specification are herewith incorporated by reference with respect to their entire disclosure content and the disclosure content specifically mentioned in this specification.

FIGURES

FIG. 2 (A) shows a plot of percentage representation of reads uniquely mapped without any mismatch to chromosome 13 in selected cell-free DNA samples according to an embodiment of the present invention; (B) shows a plot of percentage representation of reads uniquely mapped without any mismatch to chromosome 21 in selected cell-free DNA samples according to an embodiment of the present invention.

FIG. 3 (A) shows a plot of percentage representation of sequence reads uniquely mapped to bait regions on chromosome 13 (150 bp upstream-150 bp downstream) without any mismatch in selected cell-free DNA samples according to an embodiment of the present invention; (B) shows a plot of percentage representation of sequence reads uniquely mapped to bait regions on chromosome 21 (150 bp upstream-150 bp downstream) without any mismatch in selected cell-free DNA samples according to an embodiment of the present invention.

FIG. 4 (A) shows a plot of percentage representation of sequence reads uniquely mapped to TSS (500 bp upstream-1500 bp downstream) on chromosome 13 without any mismatch in selected cell-free DNA samples according to an embodiment of the present invention; (B) shows a plot of percentage representation of sequence reads uniquely mapped to TSS (500 bp upstream-1500 bp downstream) on chromosome 21 without any mismatch in selected cell-free DNA samples according to an embodiment of the present invention.

In order that the invention described herein may be more fully understood, the following example is set forth. It is for illustrative purposes only and shall not be construed as limiting this invention in any respect.

It is further understood that the present invention shall also comprise variations of the expressly disclosed embodiments to an extent as would be contemplated by a person of ordinary skill in the art.

EXAMPLES

Example 1

Performance of Prenatal Diagnosis for Detection of Fetal Chromosomal Disorders by Target Enrichment Technology Firstly, up to 15 ml of peripheral blood are taken from a pregnant woman and collected in tubes containing EDTA. Cell-free plasma is obtained by centrifugation of the blood sample. The cell-free plasma DNA is extracted from the plasma by using the QIAamp DSP DNA Blood Mini Kit (Qiagen) or QIAamp DNA Micro Kit (Qiagen).

After DNA extraction a step of target enrichment is carried out. More specifically, one or more specific DNA sequences comprising consensus nucleosome binding regions around transcriptional start sites of protein-coding genes of the chromosome(s) of interest are selectively enriched by solution-based hybrid selection technique. For this specific enrichment the SureSelect Target Enrichment System (Agilent Technologies) may be used according to the user's manual. For initiating sample preparation up to 10 ng of cell-free plasma DNA are used for prepped library production specific to the sequencing platform utilized downstream such as the Illumina sequencing instrument. The subsequent library preparation is carried out according to the corresponding manufacturer's protocol with the modification that no fragmentation by nebulization or sonication is done on the cell-free plasma DNA sample.

In parallel with library production a specific SureSelect kit containing a mixture of designed SureSelect RNA oligonucleotides is created on Agilent's web-based design tool. Table 1 shows an example of a customized kit design suitable for the detection of chromosomal aneuploidies and sex-linked genetic diseases caused by a mutation on the X chromosome. In detail, for each chromosome of interest including reference chromosome(s) hybridization probes for the regions around the transcriptional start sites (approximately 1.5 kb) of all known protein-coding genes on the respective chromosome are generated resulting in an amount of enriched DNA of about 4 Mb.

TABLE 1

Example of a customized kit design for detection of chromosomal aneuploidies and X-linked genetic diseases

| Chromosome | Protein-coding Genes (corresponding to number of hybridisation probes) (Ensembl release 55 - July 2009; www.ensembl.org/index.html) | approximately enriched kb-length per 1.5 kb around transcription start site of protein-coding genes | Syndrome or chromosomal disorder |
|---|---|---|---|
| 13 | 359 | 520 | Patau syndrome (trisomy 13) |
| 16 | 1038 | 1250 | trisomy 16 |
| 18 | 315 | 470 | Edwards syndrome (trisomy 18) |
| 21 | 265 | 390 | Down syndrome (trisomy 21) |
| X | 883 | 1250 | Turner syndrome, Triple X syndrome, X-linked genetic diseases |
| Y | 86 | 120 | XYY syndrome, sex-linked genetic diseases |
| | | 4 Mb | |

To perform the DNA-capture the size-selected library is incubated with the designed SureSelect RNA oligonucleotides, and the thereby generated RNA-DNA-hybrids are incubated with streptavidin-labeled magnetic beads in order to allow for capturing the RNA-DNA hybrids by linking them to the beads. After collecting the loaded beads by attracting them onto a magnet the beads are washed and the RNA oligonucleotides are digested whereupon only the remaining enriched DNA of interest is harvested. After final DNA amplification and estimation of the quality of the PCR products using, for example, Agilent 2100 Bioanalyzer (Agilent Technologies) the enriched pool of target DNA sequences is then subjected to sequencing by massive parallel sequencing using, for example, the 454 platform (Roche) (Margulies, M et al. 2005 Nature 437, 376-380), Illumina Genome Analyzer or SOLiD System (Applied Biosystems), which allows for sequencing of many nucleic acid molecules isolated from one human plasma DNA sample in a parallel fashion.

The subsequent bioinformatics procedure is then used to locate each of these DNA sequences on the human genome. More specifically, the short reads are collected from the sequencing instrument and aligned to the human reference genome (hg18, NCBI build 36 (GenBank accession numbers: NC_000001 to NC_000024) using several bioinformatic tools such as ELAND (Efficient Large-Scale Alignment of Nucleotide Databases). To ensure a high quality of the results, it is preferred that only those reads are considered for further analysis which are located in pre-selected genomic regions comprising consensus nucleosome binding regions of the chromosome(s) of interest and which are uniquely mapped to the human genome with only one or two mismatches against the human genome.

The resulting digital readout of nucleic acid molecules is then used for the detection of fetal chromosomal aneuploidies, e.g. trisomy 13, 18 or 21, and can likewise be used for the determination of the gender of the fetus.

An imbalance such as a chromosomal aneuploidy in a given experimental sample is revealed by differences in the number or percentage of sequences aligned to a given chromosomal region of interest as compared to the corresponding number or percentage of such sequences expected or pre-determined for a euploid human genome sample.

The present method is suitable for the detection of one or more chromosomal aneuploidies in one run, wherein the affected chromosome is typically selected from the group consisting of chromosome 21 (trisomy 21), chromosome 18 (trisomy 18), chromosome 13 (trisomy 13), and chromosome X (Turner syndrome).

The selective target enrichment sequencing method according to the present invention may also be applicable to other diagnostic applications involving qualitative and/or quantitative evaluation of serum or plasma nucleic acid contents, e.g., in oncology and transplantation medicine. For example, the afore described selective target enrichment sequencing technique on cell-free DNA may also be used to detect tumor-specific chromosomal alterations associated with specific cancer.

The principle of the invention is further described in the independent claim hereinafter, the various embodiments of the invention being the subject matter of the dependent claims.

Example 2

Performance of Prenatal Diagnosis for Detection of Trisomy 21 and Trisomy 13 by Target Enrichment Technology and Multiplexed Barcode Sequencing For the study maternal blood samples were selected from 4 singleton pregnancies. One of the pregnant women was carrying an euploid male fetus and the other three were carrying a fetus with trisomy 21, trisomy 13 and trisomy 18, respectively (Table 2, below). Up to 15 ml of peripheral venous blood were taken from these pregnant women and collected in EDTA tubes. The plasma was obtained from the blood samples by centrifugation at 1600 g at 4° C. for 10 min. To remove residual cells the plasma was additionally centrifuged at 16000 g at 4° C. for 10 min. From plasma samples the cell-free DNA was extracted from 0.8-1 ml of plasma by using the QIAamp Circulating Nucleic Acid Kit (Qiagen) according to manufacture's protocol.

Up to 10 ng of cell-free plasma DNA was then used to construct Illumina sequencing libraries. The DNA library preparation followed the Illumina standard sample preparation protocol for paired-end sequencing with a few modifications. Briefly, no fragmentation by nebulization or sonication was done on the cell-free plasma DNA samples. The library preparation was carried out according to the beta Chromatin Immunoprecipitation Sequencing (ChIP-Seq) sample preparation protocol (Illumina; Part #11257047 Rev. A) using enzymes from Fermentas (T4 DNA Polymerase, Klenow DNA Polymerase, T4 polynucleotide kinase, DNA Ligase) as well as from Finnzymes Oy (Phusion* Polymerase). The products were end-repaired and 3' non-template A's were added. To make multiplexed barcode sequencing available, DNA libraries were "tagged" with different identifiers (barcodes) during paired-end adaptor ligation. The first adaptor contained the sequencing primer sites for application read 1 and a 4 bp-identifier as well as a 'T' which is necessary for adaptor ligation. The second adaptor contained the sequencing primer sites for application read 2 and a 'T' too. The DNA libraries with barcoded samples were then additionally amplified using a 12-cycle PCR and primers containing the attachment sites for the flow cells. The adapter-ligated DNA fragments were size selected in the range of 150-300 bp using 2% agarose gel electorphoresis. A quality control and quantification of libraries were done using a High Sensitivity DNA kit on the Agilent 2100 Bioanalyzer according to the manufacturer's instructions.

To target all human exons and their associated human genomic regions corresponding to the transcription start sites (TSSs), 500 ng of libraries were incubated with the SureSelect Human All Exon Kit (Agilent Technologies) and enriched according to the manufacturer's protocol. After elution of the captured DNA fragments, the libraries were reamplified for 12-14 cycles of PCR with SureSelect Illumina-specific primers. Amplification enables accurate quantification using the Bioanalyzer High Sensitivity chip before sequencing.

The four different barcoded samples are then pooled into a single tube and clonal clusters were generated using cBOT clonal amplification system with the cBOT Paired-End Cluster Generation Kit. Following Illuminas sequencing workflow the amplified single-molecule DNA templates were sequenced using massive parallel synthesis on Illumina Genome Analyzer IIx.

The subsequent bioinformatics procedure included image analysis, base calling and alignment by using Illumina's pipeline software. For individual downstream analysis a semi-automated tag sorting strategy identified each uniquely barcoded sample. The first 32-bp of each read of each sample were aligned to the repeat-masked human genomic reference sequence NCBI build 36 (also known as hg18; GenBank accession numbers: NC_000001 to NC_000024) downloaded from UCSC Genome Browser using ELAND alignment software (GAPipeline-1.4.0 software) provided by Illumina.

The resulting digital readouts of nucleic acid molecules were then used for the detection of fetal chromosomal aneuploidies, e.g. trisomy 13 or 21, and can likewise be used for the determination of the gender of the fetus.

Initially, the total number of sequenced reads for each sample were counted. Subsequently, only sorted reads that had uniquely mapped to one location in the repeat-masked human genomic reference sequence and without any nucleotide mismatch were used for further analysis (see Table 2, below).

Figure 1:
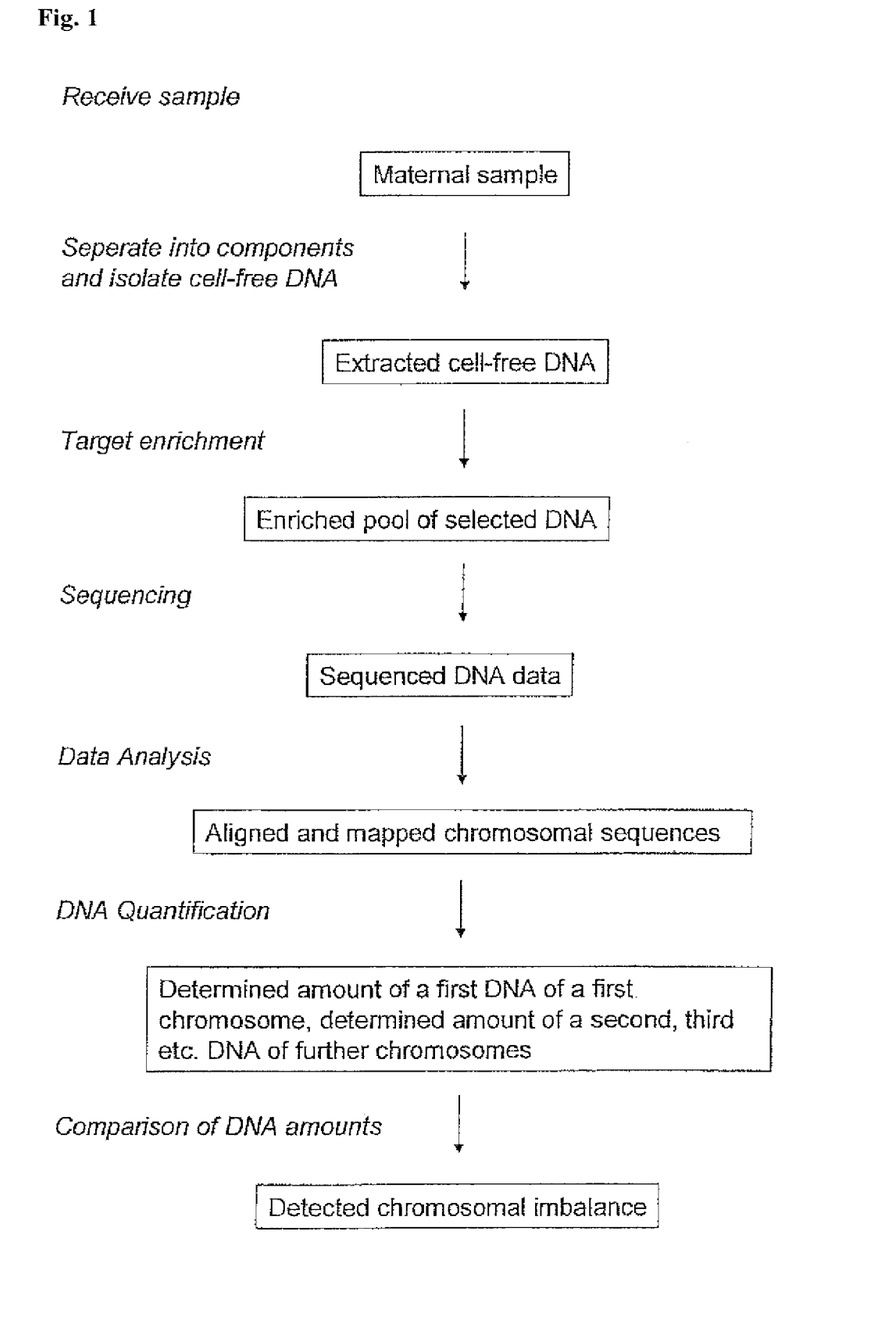
FIG. 1 shows a flowchart delineating the principle workflow of a method for performing prenatal diagnosis for the determination of a fetal chromosomal aneuploidy in a biological sample obtained from a pregnant woman according to the present invention.
Figure 2:
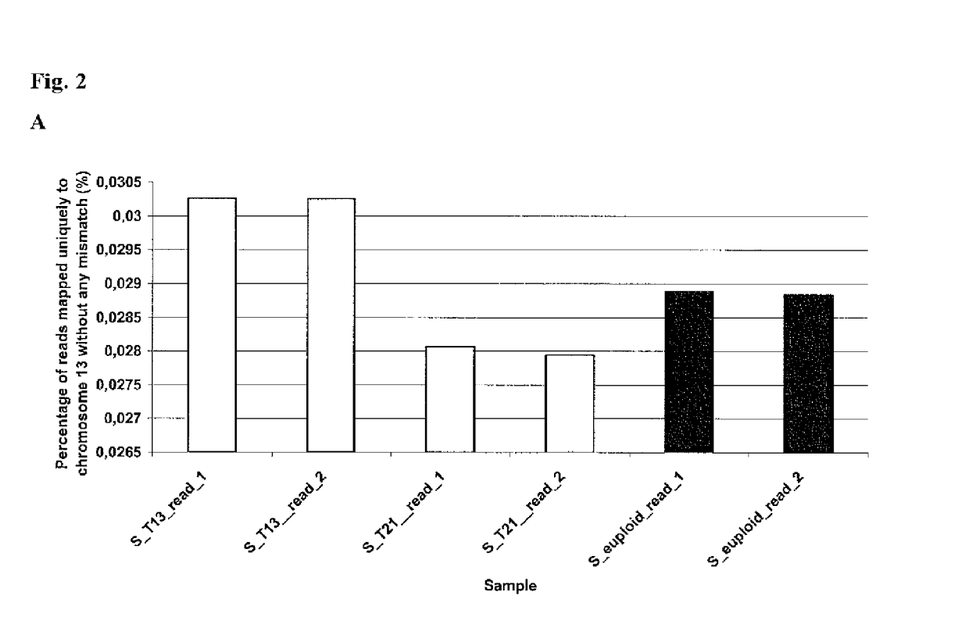

In the first place, an imbalance such as trisomy 21 and trisomy 13 in the given experimental samples was revealed by differences in the number or percentage of repeat-masked uniquely mapped reads without any mismatch of interest (originating from chromosomes 13 and 21, respectively) as compared to the corresponding number or percentage of such sequences determined for the euploid human genome sample. The expected percentage of representation of each chromosome was obtained by dividing the number of repeat-masked uniquely mapped reads without any mismatch per chromosome by the number of total repeat-masked uniquely mapped reads without any mismatch of all chromosomes. As shown in FIG. 2A, the percentage of reads uniquely mapped to chromosome 13 from sample S_T13 was higher than that from sample S_euploid with an euploid fetus as well as from sample S_T21 carrying a fetus with Trisomie 21. The percentage of reads uniquely mapped to chromosome 21 from sample S_T21 was also higher than that from sample S_euploid with an euploid fetus as well as from sample S_T13 carrying a fetus with Trisomie 13 (FIG. 2B).

Figure 3:
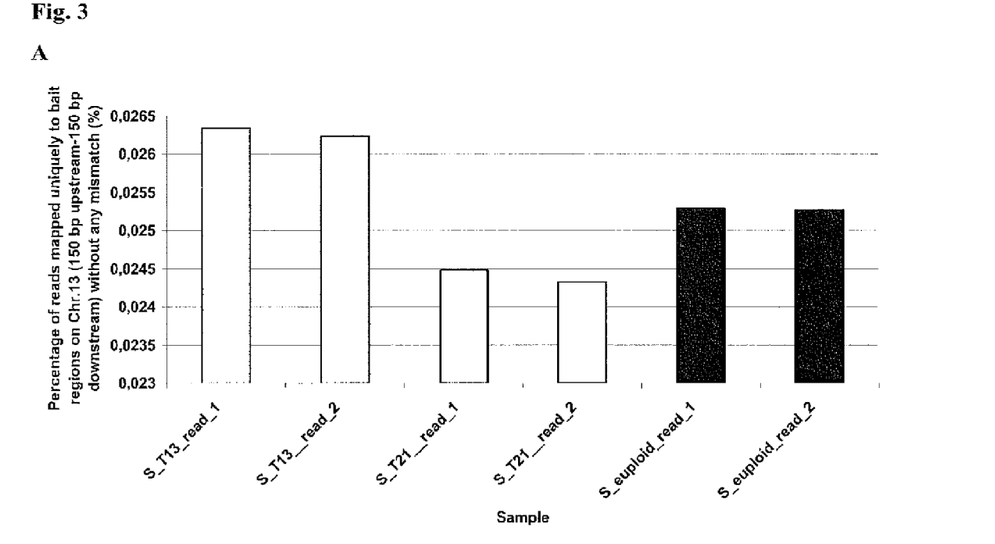

In the second place, an imbalance such as trisomy 21 and trisomy 13 in the given experimental samples was revealed by differences in the number or percentage of repeat-masked uniquely mapped reads without any mismatch aligned to a given chromosomal region of interest compared to the corresponding number or percentage of such sequences determined for the euploid human genome sample. The chromosomal region of interest was characterized by the predetermined 120 bp-bait regions (available at eArray platform by Agilent Technologies) of the SureSelect Human All Exon Kit (Agilent Technologies) plus flanking 150 bp-regions upstream and downstream located of bait regions. The expected percentage of representation of each chromosome was then obtained as described before. An overrepresentation of uniquely mapped reads was observed for chromosomes 13 and chromosomes 21 in T13 and T21 cases, respectively (FIGS. 3A and 3B).

Figure 4:
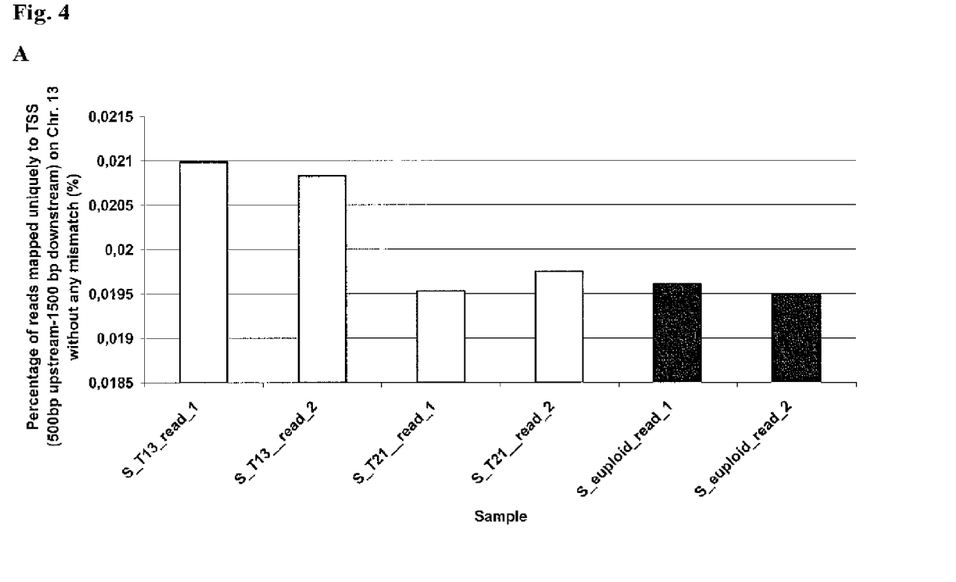

In the third place, an imbalance such as trisomy 21 and trisomy 13 in the given experimental samples was revealed by differences in the number or percentage of repeat-masked uniquely mapped reads without any mismatch aligned to a given consensus nucleosome binding region as compared to the corresponding number or percentage of such sequences expected or pre-determined for the euploid human genome sample. The consensus nucleosome binding region as used herein included sequence regions from 500 bp upstream the TSS to 1500 bp downstream the TSS. The percentage of reads uniquely mapped to chromosome 13 from sample S_T13 was higher than that from sample S_euploid with an euploid fetus as well as that from sample S_T13 (FIG. 4A). The percentage of reads uniquely mapped to chromosome 21 from sample S_T21 was only higher than that from sample S_T13 and not higher than that from sample S_euploid with an euploid fetus (FIG. 4B).

The present method was suitable for the detection of one or more chromosomal aneuploidies in one run, wherein the affected chromosome is typically selected from the group consisting of chromosome 21 (trisomy 21), chromosome 18 (trisomy 18), chromosome 13 (trisomy 13), and chromosome X (Turner syndrome).

Figure 5:
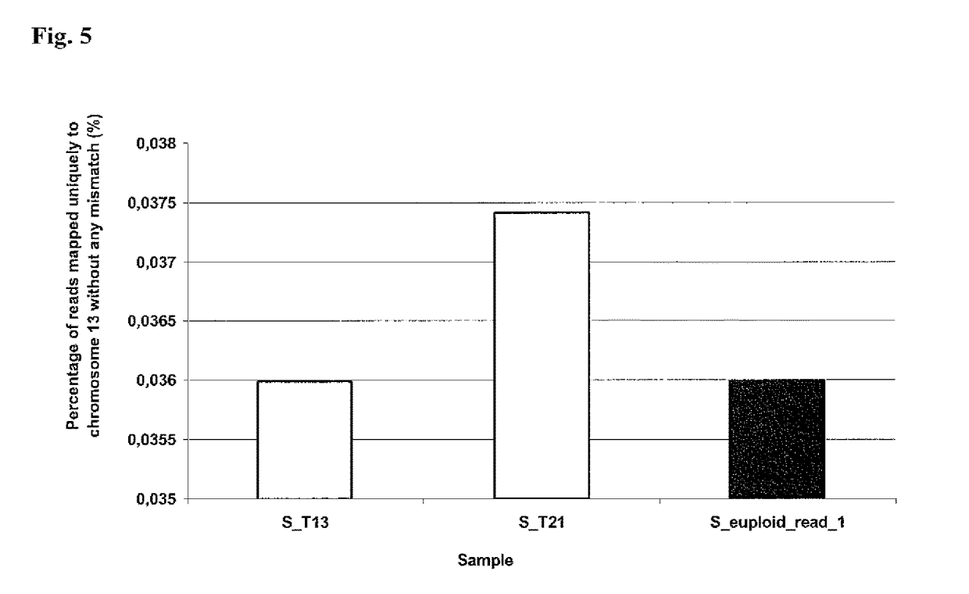
FIG. 5 shows a plot of percentage representation of chromosome 13 sequence reads in selected cell-free DNA samples according to earlier results using shotgun sequencing strategy without enrichment process.

In comparison to previous experiments (FIG. 5 and Table 3, below) using solely shotgun sequencing this method was appropriate to even detect a trisomy 13.

Furthermore, the described method tends to result in reduction of storage capacities for raw data as well as for mapping and alignment of generated sequence reads.

TABLE 2

(i) Summary of clinical data and number of sequence reads of Example 2 "Performance of prenatal diagnosis for detection of Trisomy 21 and Trisomy 13 by target enrichment technology and multiplexed barcode sequencing"

| Sample | Karyotype | Gestational Age (weeks + days) | Total no. of sequence reads_read1 | Total no. of sequence reads_read2 |
|---|---|---|---|---|
| S_T13 | 47XY + 13 | 13 + 5 | 5005094 | 5005094 |
| S_T21 | 47XY + 21 | 13 + 0 | 6739231 | 6739231 |
| S_euploid | 46XY | 16 + 0 | 3415786 | 3415786 |

| Sample | Total no. of uniquely mapped reads without any mismatch_read1 | Total no. of uniquely mapped reads without any mismatch_read2 | No. of uniquely mapped reads without any mismatch of chromosome 13_read1 | No. of uniquely mapped reads without any mismatch of chromosome 13_read1 | No. of uniquely mapped reads without any mismatch of chromosome 21_read1 | No. of uniquely mapped reads without any mismatch of chromosome 21_read2 |
|---|---|---|---|---|---|---|
| (ii) Summary of number of sequence reads of Example 2 | | | | | | |
| S_T13 | 2856635 | 2745340 | 8643 | 83057 | 32290 | 31010 |
| S_T21 | 3913173 | 3761195 | 109842 | 105110 | 45647 | 44115 |
| S_euploid | 1959738 | 1895396 | 56616 | 54658 | 2191 | 21186 |
| (iii) Summary of number of sequence reads of a chromosomal region of interest (characterized by the predetermined 120 bp-bait regions of the SureSelect Human All Exon Kit plus flanking 150 bp-regions upstream and downstream located of bait regions) of Example 2 | | | | | | |
| S_T13 | 1599317 | 1530800 | 42125 | 40162 | 17060 | 16256 |
| S_T21 | 2215860 | 2120634 | 54244 | 51598 | 24433 | 23345 |
| S_euploid | 1091265 | 1051800 | 27601 | 26577 | 11679 | 11303 |
| (iv) Summary of number of sequence reads aligned to a given consensus nucleosome binding region including sequence regions from 500 bp upstream the TSS To 1500 bp downstream the TSS (Example 2) | | | | | | |
| S_T13 | 202723 | 196213 | 4254 | 4087 | 2755 | 2652 |
| S_T21 | 282640 | 273834 | 5520 | 5408 | 3951 | 3814 |
| S_euploid | 135892 | 131693 | 2665 | 2567 | 1880 | 1857 |

TABLE 3

Summary of number of sequence reads of previous experiments using shotgun sequencing method

| Sample | Total no. of sequence reads | Total no. of uniquely mapped reads without any mismatch | No. of uniquely mapped reads without any mismatch of chromosome 13 | No. of uniquely mapped reads without any mismatch of chromosome 21 |
|---|---|---|---|---|
| S_T13 | 16611762 | 5992776 | 215666 | 73885 |
| S_T21 | 26137898 | 10752119 | 402319 | 141130 |
| S_euploid | 20289419 | 7928946 | 285433 | 99306 |

The invention claimed is:

1. A method for determining a fetal chromosomal aneuploidy in a biological sample of a pregnant female individual, wherein the biological sample includes nucleic acid molecules, the method comprising:
    (a) selecting for and isolating from a biological sample of a pregnant female individual one or more target sequences of DNA molecules present in the biological sample using sequence-specific selection of the target sequences, wherein said target sequences comprise DNA sequences including sequence regions located from 500 bp upstream to 1500 bp downstream of a transcription start site (TSS);
    (b) amplifying said selected target sequences;
    (c) sequencing said amplified selected target sequences, allotting each target sequence to a chromosome of the genome and identifying the unique allotted target sequences, wherein each identified unique allotted target sequence maps to a single chromosome;
    (d) determining a first amount for each of one or more first chromosomes identified on the basis of said unique allotted target sequences originating from said one or more first chromosomes;
    (e) determining a second amount for each of one or more second chromosomes identified on the basis of said unique allotted target sequences originating from said one or more second chromosomes; and
    (f) determining based on the said first and second amount a fetal chromosomal aneuploidy of one or more of said first chromosomes.

2. The method of claim 1, wherein step (f) further comprises:
    (i) determining a parameter from said first amount relative to said second amount;
    (ii) comparing the parameter to a corresponding cut off control value; and based on the comparison, determining whether or not there is a difference allowing for the prediction of a fetal chromosomal aneuploidy of one or more of said first chromosomes.

3. The method of claim 1, wherein said biological sample is a maternal blood sample.

4. The method of claim 3, wherein said blood sample is a sample of maternal blood plasma or maternal blood serum.

5. The method of claim 1, wherein said biological sample is a urine sample or a saliva sample.

6. The method of claim 1, wherein said one or more first chromosomes are selected from the group consisting of chromosome 21, chromosome 18, chromosome 13, chromosome X, and chromosome Y.

7. The method of claim 1, wherein step (a) comprises contacting the biological sample with a nucleic acid probe specific for each target sequence.

8. The method of claim 7, wherein the nucleic acid probe comprises RNA or DNA.

9. The method of claim 7, wherein the nucleic acid probe is biotinylated.

\* \* \* \* \*